United States Patent [19]
Ichiro

[11] Patent Number: 5,623,746
[45] Date of Patent: Apr. 29, 1997

[54] TOOTH-BRUSHING MACHINE

[75] Inventor: Sugimoto Ichiro, Yokkaichi, Japan

[73] Assignee: Euronica Corporation, Hyogo, Japan

[21] Appl. No.: 507,338

[22] PCT Filed: Feb. 14, 1994

[86] PCT No.: PCT/JP94/00220

§ 371 Date: Aug. 14, 1995

§ 102(e) Date: Aug. 14, 1995

[87] PCT Pub. No.: WO94/17690

PCT Pub. Date: Aug. 18, 1994

[30] Foreign Application Priority Data

Feb. 15, 1993 [JP] Japan .................................. 5-050109

[51] Int. Cl.$^6$ ........................................... A46B 13/04
[52] U.S. Cl. ........................ 15/22.2; 15/167.1; 15/201; 15/205.2; 601/162
[58] Field of Search ..................... 15/22.1, 22.2, 15/24, 201, 205.2, 167.1; 401/271, 284; 601/162

[56] References Cited

U.S. PATENT DOCUMENTS

| 4,346,492 | 8/1982 | Solow | 15/22.1 |
| 4,534,340 | 8/1985 | Kerr et al. | 15/22.1 |
| 4,630,326 | 12/1986 | Stevens | 15/22.1 |
| 4,671,259 | 6/1987 | Kirchner | 601/162 |
| 4,787,847 | 11/1988 | Martin et al. | 15/22.1 |
| 5,327,608 | 7/1994 | Kosakewich | 15/22.1 |

*Primary Examiner*—David Scherbel
*Assistant Examiner*—James F. Hook
*Attorney, Agent, or Firm*—Ilya Zborovsky

[57] ABSTRACT

Large-diameter cylindrical portion (3) is formed in water passage (2) of a water-spraying nozzle (1) in the vicinity of the tip portion of said nozzle. Piston (5) which is housed in aforementioned cylindrical portion (3) is driven in a reciprocating manner, so that the tip portion of bristle bundle (4) which is implanted in the front surface of aforementioned piston (5) is caused to move in and out via water-spraying opening (6) located at the tip of aforementioned nozzle (1).

7 Claims, 3 Drawing Sheets

TOOTH-BRUSHING MACHINE

FIELD OF THE INVENTION

The present invention concerns a tooth-brushing machine which is suitable for the prevention and treatment of alveolar pyorrhea.

BACKGROUND OF THE INVENTION

In recent years, a brushing method has been developed which makes it possible [a] to prevent alveolar pyorrhea, [b] to stop the progression of alveolar pyorrhea, or [c] to regenerate alveolar bone which has already been dissolved as a result of alveolar pyorrhea, by brushing vigorously for a long period of time with the bristle tips of the toothbrush inserted into the gingival sulcus (reference: Tsuneo Katayama, "Shiso Noro" ["Alveolar Pyorrhea"], Asahi Shinbunsha). FIG. 4(a) is a sectional view of a tooth sustaining alveolar pyorrhea, and FIG. 4(b) is a sectional view of a normal tooth. Even in the case of a healthy tooth, there is a gingival sulcus C with a depth of approximately 1 to 2 mm between the tooth A and the gingiva B. If bacteria multiply inside this gingival sulcus C, plaque consisting of said bacteria and their waste products will accumulate so that the gingival sulcus C eventually becomes blocked. As a result, air cannot reach inside of the gingival sulcus, and this leads to the multiplication of anaerobic bacteria which cause alveolar pyorrhea. These organisms invade the area between the gingiva B and the tooth root A2, and thus cause an inflammation. This inflammation is alveolar pyorrhea; when such alveolar pyorrhea occurs, pockets D are formed inside the gingival sulcus C, and the alveolar bone E which supports the tooth root A2 gradually dissolves.

Places from which it is especially difficult to remove plaque include the interdental gingival sulcus C and pockets D formed inside the gingival sulcus C. It is extremely difficult for the bristle tips of conventional toothbrushes to reach these areas. Accordingly, in the new brushing method mentioned above, a toothbrush in which bundles of stiff bristles are implanted in a single row is used. This toothbrush is pressed against the designated area, and a single bundle of stiff bristles is inserted into the gingival sulcus. The toothbrush is then caused to vibrate with a fine vibratory action while the bristle tips are allowed to rest in the aforementioned position. In this way, the bristle tips can reach the inside of the gingival sulcus C and the inside areas of the aforementioned pockets D, which could not be reached in the case of conventional toothbrushes because of interference by other bristles. Thus, by agitating the accumulated viscous plaque (which does not readily dissolve in water) with the bristle tips, it is possible to supply oxygen to the anaerobic bacteria which cause alveolar pyorrhea, thereby killing said bacteria.

However, in the case of the abovementioned brushing method, a special toothbrush with a small number of stiff bristles is used, and brushing is performed vigorously in each individual location without altering the position of the bristle tips. Furthermore, the patient is required to perform toothbrushing for a long period of time, i.e., 1 to 3 hours per day. As a result, the patient's arm becomes tired, and the treatment requires an excessive amount of time, so that it is not easy to continue this treatment on a long-term basis.

Furthermore, although an electrically driven toothbrush may be used in order to shorten the brushing time, conventional electric toothbrushes are designed so that the bristles are caused to move in the lateral direction rather than in the longitudinal direction. Accordingly, the bristle bundles are bent so that the bristle tips constantly move in a direction which causes said bristle tips to be withdrawn. As a result, it is absolutely impossible to insert the bristle tips into the interdental gingival sulcus C or into the aforementioned pockets D as described above. It would also be conceivable to use an oral cavity cleaning device employing a jet water current in order to remove plaque from the gingival sulcus C or pockets D. However, as was described above, this plaque will not dissolve in water, and has a strong gumminess which causes said plaque to adhere firmly to the surfaces of the teeth. Accordingly, it is difficult to strip this plaque away using only the jet water current of an oral cavity cleaning device.

SUMMARY OF THE INVENTION

The present invention was devised in light of the above-mentioned problems; the object of the present invention is to provide a tooth-brushing machine which uses a motive force to perform brushing inside the aforementioned interdental gingival sulcus C and pockets D (which cannot be accomplished using conventional oral cavity cleaning devices or electric toothbrushes, and which has been possible in the past only by the manual use of a toothbrush with a special shape), and which thus greatly reduces the time and effort conventionally required for such brushing, so that alveolar pyorrhea can be effectively prevented or treated.

In order to achieve the abovementioned object, the tooth-brushing machine of the invention described in Claim 1 is designed as follows: i.e., a large-diameter cylindrical portion is formed in a water passage located near the tip of a water-spraying nozzle, and a means is provided for driving (in a reciprocating manner) a piston which is housed in said cylindrical portion, so that the tip portion of a bundle of bristles implanted in the front surface of the aforementioned piston moves in and out via the water-spraying opening at the tip of the aforementioned nozzle. The means used to drive the aforementioned piston in a reciprocating manner may be a small motor and cam mechanism such as those used in an ordinary electric toothbrush; alternatively, as is shown in FIG. 1, a solenoid of the type used in vibrators, etc., may be used. Furthermore, as is shown in FIG. 2 or FIG. 3, the tooth-brushing machine of the invention described in Claim 2 is designed so that a mechanism which creates a pulsating water current is provided as a means for driving the abovementioned piston in a reciprocating manner, and the motive force of this mechanism is transmitted to the piston using water as a medium.

In the invention described in Claim 1, the bristle bundle moves in a reciprocating manner in the longitudinal direction of said bristle bundle, i.e., in the direction in which the bristle tips are facing. Accordingly, the bristle tips can be inserted straight into the aforementioned gingival sulcus C or pockets D. Furthermore, since the bristle bundle consists of a single bundle of bristles and is therefore slender, the bristle tips can be inserted without undue effort into narrow, deep areas such as the interdental gingival sulcus C, which cannot be reached by the bristle tips of an ordinary toothbrush. Accordingly, the bristle tips can be accurately placed against the desired affected area. Moreover, since the bristle bundle is driven by a motive force, the patient's arm does not become tired so quickly, and brushing which required a long time in the case of the aforementioned manual brushing process can be completed in a short time.

Furthermore, since the bristle bundle emerges from the aforementioned nozzle spray opening together with a water current, the plaque stripped from tooth surfaces by brushing can be washed out of the gingival sulcus C or pockets D together with food debris. Moreover, the area of sliding contact between the nozzle spray opening and the bristle bundle is lubricated and cleaned by the aforementioned water current. Accordingly, there is no danger that the bristle bundle will become soiled or that the aforementioned area of sliding contact will become clogged with foreign matter so that faulty operation occurs. In addition, the nozzle spray opening can be caused to act as a guide so that bending or spreading of the bristles is prevented. Moreover, since the bristle bundle is constantly cooled by the aforementioned water current, softening deformation of the bristles due to frictional heat or body heat can be prevented.

Furthermore, if the constitution described in Claim 2 is used, the pulsating water current of an oral cavity cleaning device of the type widely used in the past can be utilized to drive the bristle bundle. Accordingly, there is no need to install a separate driving mechanism consisting of a motor and cam mechanism, etc., in order to drive the bristles. Moreover, the water current can be caused to pulsate at a high speed, e.g., 30 pulses per second, and the small, light-weight bristle bundle is thoroughly capable of following this high-speed pulsation. Accordingly, brushing conventionally requiring one hour can be accomplished in only a few minutes. Furthermore, since a water current is utilized, there is no danger that the impact force of the bristle tips will be excessive, even if the nozzle is placed in close proximity to the affected area. Accordingly, there is no danger that the affected area will be injured.

BRIEF DESCRIPTION OF THE DRAWINGS

FIG. 2 illustrates another embodiment of the present invention.

FIG. 3 illustrates still another embodiment of the present invention.

FIG. 4 is an explanatory diagram which illustrates the present invention.

DETAILED DESCRIPTION OF THE PREFERRED EMBODIMENTS

Figure 1:
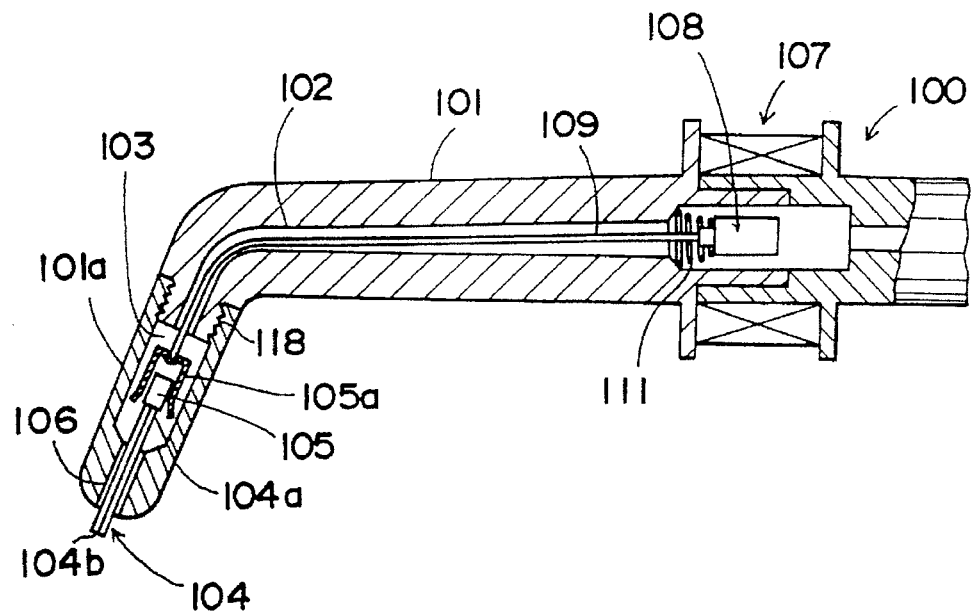
FIG. 1 is a longitudinal section which illustrates the essential parts of one embodiment of the present invention.

FIG. 1 illustrates one embodiment of the invention described in Claim 1. Here, the tip portion of spray nozzle 1 made of plastic is bent in order to facilitate brushing of the back side of the teeth. Large-diameter cylindrical portion 3 is formed in water passage 2 of nozzle 1 near the tip of nozzle 1, and a single bundle of bristles is implanted in the front surface of piston 5 which is housed inside aforementioned cylindrical portion 3. Piston 5 is connected to movable iron core 8 of solenoid 7 (installed in the base end portion of nozzle 1 by means of flexible wire 9 such as a slender piano wire, etc., and a pulsating electric current is applied to solenoid 7, so that [piston 5] is driven back and forth inside cylindrical portion 3 in a reciprocating manner, thus causing bristle bundle 4 to move in and out via water-spraying opening 6 of nozzle 1. In the present embodiment, holder 10 which allows attachment and detachment of piston 5 is installed on the tip of aforementioned wire 9, and tip portion 1a of nozzle 1 can be removed by means of screw 18, so that bristle bundle 4 can easily be replaced when said bristle bundle 4 has become deformed as a result of fatigue. Furthermore, 11 indicates a spring which is used in order to apply a back pressure to movable iron core 8 or piston 5. Tap water is supplied to the base end portion of nozzle 1 via a flexible tube, so that water flows out of the tip of the nozzle as bristle bundle 4 moves in and out. This water current washes food debris and plaque from the gingival sulcus C, and also acts to clean and cool the bristles themselves, and to provide lubrication between the bristles and the nozzle.

Thus, in the invention described in Claim 1, slender bristle bundle 4 is driven back and forth in the longitudinal direction of said bristle bundle. Accordingly, the bristle tips can be inserted without undue effort into narrow, deep locations such as the aforementioned interdental gingival sulcus C or pockets D, which cannot be reached by the bristle tips of an ordinary toothbrush. In addition, the bristle tips of bristle bundle 4 can be accurately placed against areas affected by alveolar pyorrhea. Furthermore, since bristle bundle 4 is small and light in weight, and since the means used to transmit the motive force from the driving source to bristle bundle 4 may also have a slender bent shape such as that of remote control wire 9 or tube 1, etc., the bristle tips can easily be applied to any desired location inside the oral cavity (e.g., to the backs of teeth or back molars, etc.). Moreover, since bristle bundle 4 is caused to emerge from the tip of nozzle 1 together with a water current, the plaque stripped from the teeth during brushing can be washed from the aforementioned gingival sulcus or pockets; furthermore, since the area of sliding contact between bristle bundle 4 and water-spraying opening 6 of nozzle 1 is lubricated and cleaned by the aforementioned water current, there is no danger that bristle bundle 4 will become soiled, or that water-spraying opening 6 will become clogged with foreign matter so that faulty operation occurs. In addition, since the aforementioned water current constantly cools bristle bundle 4, softening deformation of the bristles caused by frictional heat or body heat can be prevented.

Figure 2A:
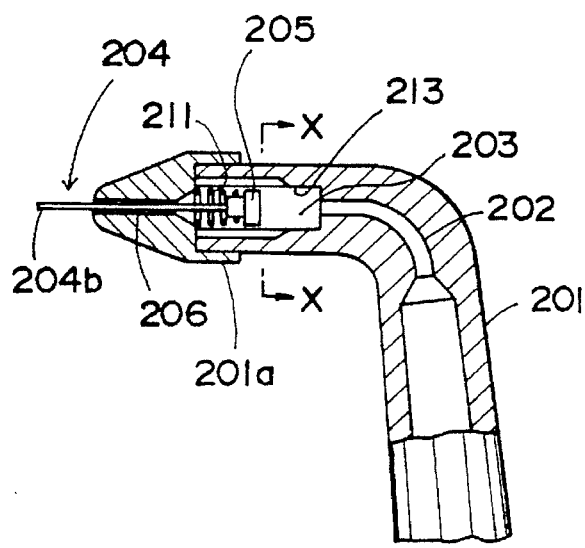
FIG. 2(a) is a longitudinal section which shows essential parts.
Figure 2B:
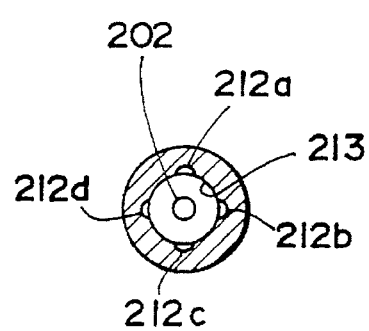
FIG. 2(b) is a sectional view along line X—X in FIG. 2(a).

Next, FIG. 2 illustrates one embodiment of the invention described in Claim 2. Here, large-diameter cylindrical portion 3 is formed in water passage 2 near the tip of nozzle 1 to which water at a constant pressure is supplied. Piston 5 which has a single bundle of bristles 4 implanted in its front surface is inserted into aforementioned cylindrical portion 3, and grooves which run in the axial direction are formed in the circumferential wall of the forward half of cylindrical portion 3 as shown by the sectional view in FIG. 2(b). When piston 5 is caused to reach the forward half of cylindrical portion 3 by the aforementioned water pressure, the water escapes in the forward direction via grooves 12, so that piston 5 is pushed back into the rear half of cylindrical portion 3 by spring 11. Piston 5 is then again pushed in the forward direction by the water pressure. Thus, even if the water pressure is constant, piston 5 oscillates backward and forward inside cylindrical portion 3, so that a pulsating water current and the tip portion of bristle bundle 4 alternately emerge from water-spraying opening 6 of nozzle 1. Furthermore, in regard to the means used to supply water at a constant pressure, tap water pressure may be applied to the base end portion of nozzle 1 via a flexible tube. However, it would also be possible to use a pressure pump to construct a water pressure source that could be used in common by a multiple number of persons.

Figure 3A:
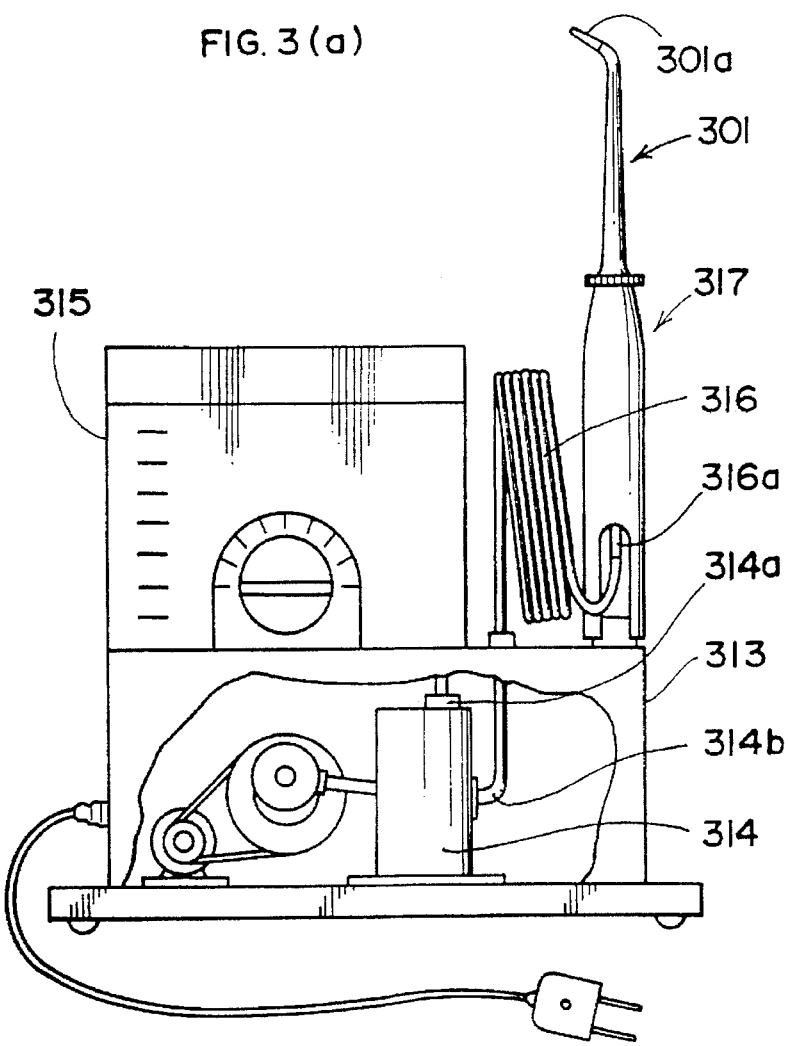
FIG. 3(a) is an overall front view of said embodiment.
Figure 3B:
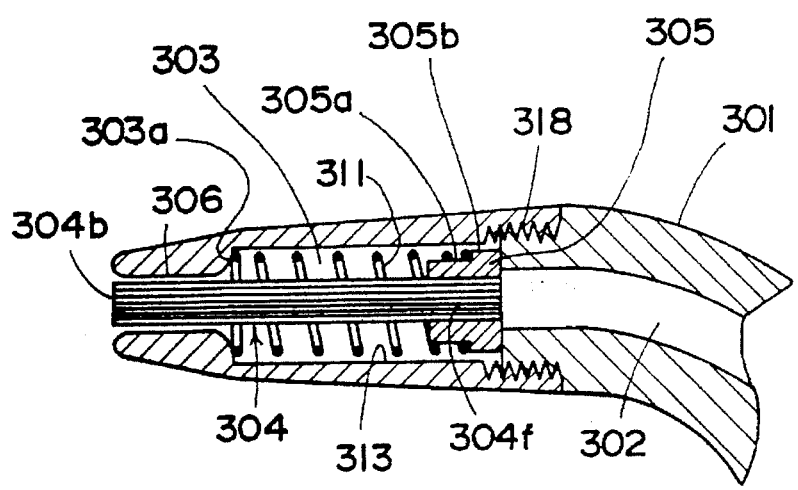
FIG. 3(b) is a longitudinal section which illustrates essential parts of said embodiment.
Figure 4A:
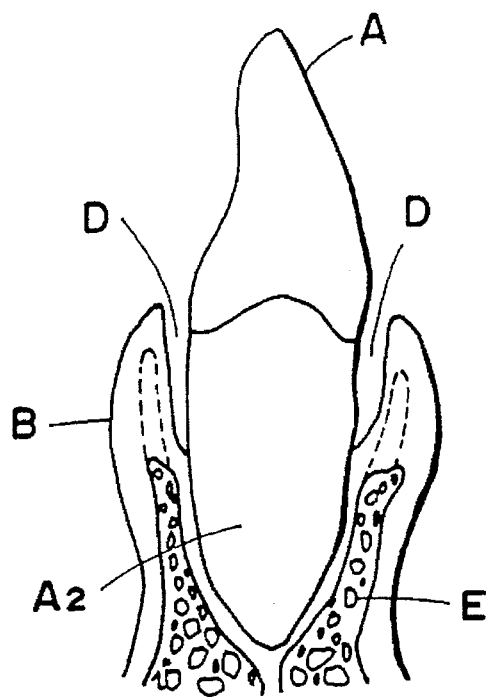
FIG. 4(a) is a sectional view of a tooth suffering from alveolar pyorrhea.
Figure 4B:
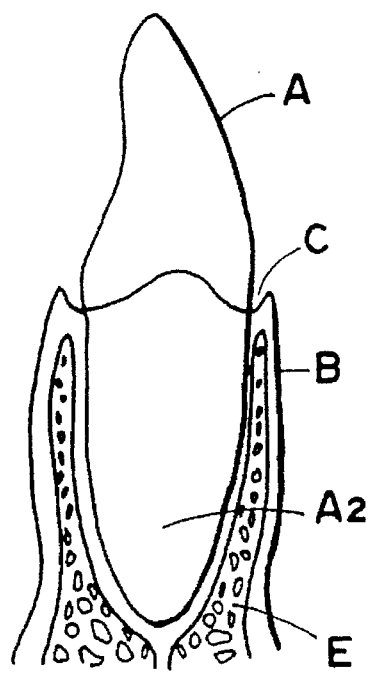
FIG. 4(b) is a sectional view of a normal tooth.

Next, FIG. 3 illustrates another embodiment of the invention described in Claim 2. In the embodiment illustrated in FIG. 2, the means used to create a pulsating water current was installed on the side of the nozzle; in the present embodiment, on the other hand, this means is installed on the side of the main body 13 of the tooth-brushing machine. Specifically, the present embodiment is characterized by that the water in tank 15 is pulsated by pump 14, and supplied to nozzle 1 via flexible tube 16. Here, the structure of a conventional oral cavity cleaning device is used "as is" as main body 13 of the tooth-brushing machine. In FIG. 3, 17 indicates a handle part which contains a manually operated water current cut-off valve, and which has nozzle 1 inserted into the tip end of said handle part. As is shown in FIG. 3(b), piston 5 which has bristle bundle 4 implanted in its front surface is inserted loosely into water passage 2 in the vicinity of the tip of nozzle 1, and the system is arranged so that the tip portion of bristle bundle 4 moves in and out of water-spraying opening 6 of nozzle 1 together with a water current. Furthermore, spring 11 which is used to retract bristle bundle 4 into nozzle 1 by pushing piston 5 backward when the water pressure pulse is "off" is installed inside cylindrical portion 3. Spring 11 improves the brushing effect by increasing the stroke of bristle bundle 4, and also serves to prevent bristle bundle 4 from being caught between the teeth when the brushing position is altered by successively moving nozzle 1. However, even if spring 11 is omitted, bristle bundle 4 will be retracted by the recoil so that said bristle bundle undergoes a reciprocating motion. Accordingly, spring 11 is not absolutely necessary.

Furthermore, tip portion 1a of nozzle 1 is designed so that said tip portion can be attached to or detached from nozzle main body 1 by means of screw 18, in order to allow replacement of bristle-equipped piston 5. In addition, bristle bundle 4, which consists of a nylon or polyester, etc., is passed through piston 5 (which is a cylindrical piston equipped with a flange), and the rear end portion of said bristle bundle is fastened to piston 5 by means of an adhesive agent or pressure bonding. Furthermore, piston 5 is guided in the correct attitude in the forward-backward direction by sliding contact between bristle bundle 4 and water-spraying opening 6 of the nozzle. Accordingly, there is no need for piston 5 to have a sliding contact surface with the inner wall of cylindrical portion 3. Thus, piston 5 may have a simple shape consisting only of a cylindrical portion which holds bristle bundle 4 and a flange portion which receives the water pressure and spring 11. The impact force of bristle bundle 4 can be appropriately selected by adjusting the clearance between the circumferential rim of the flange portion of piston 5 and the inner surface of aforementioned cylindrical portion 3 [of water passage 2].

Thus, in the invention described in Claim 2, an oral cavity washing device of the type used widely in the past can be used "as is" as main body 13 of the tooth-brushing machine. In addition, the water current used to wash the oral cavity can also be used to drive bristle bundle 4; accordingly, there is no need to install a separate bristle driving mechanism, and the structure of the device can therefore be simplified. Furthermore, in the creation of the aforementioned pulsating water current, a high-speed pulsation (e.g., 30 pulses per second) is possible, and since small, light-weight piston 5 is thoroughly capable of following such a high-speed pulsation, brushing conventionally requiring an hour or more can be accomplished in only a few minutes. Moreover, piston 5 is propelled by the viscosity of the aforementioned water current; accordingly, even if nozzle 1 is placed too close to the affected area, the impact force of the bristle tips will not become excessive as it does in the case of direct driving. Thus, there is no danger of injuring the affected area.

I claim:

1. A tooth brushing machine, comprising a hollow nozzle having a tip with a water-spraying opening; a single bundle of bristles extending through said water-spraying opening; and means for reciprocating said single bundle of bristles in said water-spraying opening so as to move said single bundle of bristles in and out of said water-spraying opening to act efficiently on user's teeth, said water spraying opening and said bundle of bristles being formed so as to form between said bundle of bristles and an inner surface of said opining a gap through which water is sprayed outwardly from said water-spraying opening around said reciprocating single bundle of bristles to act efficiently on user's teeth.

2. A tooth-brushing machine as defined in claim 1, wherein said nozzle has a substantially cylindrical chamber; and further comprising a piston located in said chamber, said means being means for creating a pulsating water current which provides a reciprocation of said piston and thereby a reciprocation of said single bundle of bristles.

3. A tooth-brushing machine as defined in claim 2, wherein said chamber has a chamber portion located forwardly of said piston and a chamber portion located rearwardly of said piston, said nozzle further having at least one groove communicating said rearward portion of said chamber with said forward portion of said chamber, so that when said piston moves to its forward position, the water from said rearward portion of said chamber flows into said forward portion of said chamber and thereby pushes said piston backwards.

4. A tooth-brushing machine as defined in claim 3, wherein said nozzle is provided with a plurality of said grooves which are spaced from one another in a circumferential direction.

5. A tooth-brushing machine as defined in claim 3, wherein said groove extends radially outwardly beyond a surface which bounds said chamber.

6. A tooth-brushing machine as defined in claim 1, wherein said tip of said nozzle has an axis, said tip of said nozzle, said single bundle of bristles, and said piston being arranged so that said single bundle of bristles moves in and out in an axial direction of said tip and the water flows around said single bundle of bristles and out of said tip of said nozzle also in the axial direction of said tip.

7. A tooth brushing machine comprising a hollow nozzle having a tip with a water-spraying opening communicating an interior of said nozzle with an exterior a single bundle of bristles extending through said water-spraying opening and means for reciprocating said bundle of bristles in said water-spraying opening so as to move said single bundle of bristles in and out of said water-spraying opening whereby alternatingly when said bundle of bristles is moved in said water-spraying opening said bundle of bristles acts efficiently on user's teeth, while when said bundle of bristles is moved out said water-spraying opening water is sprayed outwardly through said water-spraying opening to act efficiently on user's teeth.

* * * * *